(12) United States Patent
Brown

(10) Patent No.: US 12,100,509 B2
(45) Date of Patent: Sep. 24, 2024

(54) REMOTE ANALYTE TESTING SYSTEM

(71) Applicant: Invent.ly LLC, Woodside, CA (US)

(72) Inventor: Stephen J Brown, Woodside, CA (US)

(73) Assignee: Invent.ly LLC, Woodside, CA (US)

( * ) Notice: Subject to any disclaimer, the term of this patent is extended or adjusted under 35 U.S.C. 154(b) by 0 days.

(21) Appl. No.: 18/344,558

(22) Filed: Jun. 29, 2023

(65) Prior Publication Data

US 2023/0360791 A1 Nov. 9, 2023

Related U.S. Application Data

(60) Division of application No. 17/947,968, filed on Sep. 19, 2022, now Pat. No. 11,728,032, which is a division of application No. 17/234,009, filed on Apr. 19, 2021, now Pat. No. 11,450,430, which is a continuation-in-part of application No. 16/683,734, filed on Nov. 14, 2019, now Pat. No. 10,998,100, which is a division of application No. 16/279,246, filed on Feb. 19, 2019, now Pat. No. 10,506,171, which is a continuation of application No. 15/955,233, filed on Apr. 17, 2018, now Pat. No. 10,362,232, which is a division of application No. 14/588,032, filed on Dec. 31, 2014, now Pat. No. 9,986,165.

(51) Int. Cl.
*G16H 40/67* (2018.01)
*G01N 21/84* (2006.01)
*G16H 10/40* (2018.01)
*H04N 7/18* (2006.01)
*H04N 23/63* (2023.01)

(52) U.S. Cl.
CPC ......... *G16H 40/67* (2018.01); *G01N 21/8483* (2013.01); *G16H 10/40* (2018.01); *H04N 7/18* (2013.01); *H04N 23/63* (2023.01); *G01N 2201/12* (2013.01)

(58) Field of Classification Search
CPC ........ G16H 40/67; G16H 10/40; G16H 30/40; G01N 21/8483; G01N 2201/12; H04N 5/23293; H04N 7/18; H04N 5/23206; H04N 7/183
USPC ..................................................... 348/207.11
See application file for complete search history.

(56) References Cited

U.S. PATENT DOCUMENTS

| | | | |
|---|---|---|---|
| 2012/0120220 A1* | 5/2012 | Al-Moosawi | G16H 30/20 348/E7.085 |
| 2018/0166155 A1* | 6/2018 | Pulitzer | G16H 20/10 |
| 2021/0373008 A1* | 12/2021 | Yaghoubi | H04N 23/62 |

* cited by examiner

*Primary Examiner* — Giovanni Astacio-Oquendo
(74) *Attorney, Agent, or Firm* — Donald R. Boys; Central Coast Patent Agency LLC

(57) ABSTRACT

A system has a device for capturing biological data from a subject, a machine-readable code associated with the device, an image capturing apparatus with internet connectivity, an image processing unit to interpret the captured biological data, and an internet-connected data repository for storing the interpreted biological data.

10 Claims, 7 Drawing Sheets

REMOTE ANALYTE TESTING SYSTEM

CROSS-REFERENCE TO RELATED DOCUMENTS

The instant case is a divisional of case Ser. No. 17/947,968, filed on Sep. 19, 2022, which is a divisional of case Ser. No. 17/234,009, filed Apr. 19, 2021, now issued as U.S. Pat. No. 11,450,430 on Sep. 20, 2022, which is a continuation-in-part from case Ser. No. 16/683,734, filed Nov. 14, 2019, now issued as U.S. Pat. No. 10,998,100 on May 4, 2021, which is a divisional application of Ser. No. 16/279,246 filed Feb. 19, 2019, now issued as U.S. Pat. No. 10,506,171 on Dec. 10, 2019, which is a continuation application claiming priority to Ser. No. 15/955,233, filed Apr. 17, 2018, now issued as U.S. patent Ser. No. 10/362,232 on Jul. 23, 2019, which is a divisional application of U.S. Ser. No. 14/588,032, filed Dec. 31, 2014, now issued as U.S. Pat. No. 9,986,165 on May 29, 2018. All disclosure of the parent cases is incorporated at least by reference.

BACKGROUND OF THE INVENTION

1. Field of the Invention

The present invention is in the field of remote testing and pertains particularly to methods and apparatus for real-time mitigation of remote test processes.

2. Discussion of the State of the Art

In the field of remote testing, including medical testing, persons may purchase test host reaction devices commonly referred to as test mediums in the art, that are designed to accept a specimen for remote testing where elements such as reactive substances preloaded into the device react with the introduced specimen to produce a measurable test result. The term remote implies that the test process is performed by a user at the user's location as opposed to a hospital or clinical environment. In current art, the process is somewhat commonly practiced with a smart phone executing a software application and a peripheral device attached to the smart phone adapted to accept the test medium for imaging using the phone's camera. Such remote testing and result determinations are made locally by the user from information processed on the phone.

Many processes detect analytes using chromatography, which is a well-established technology. Chromatography may be used to detect substances in water, blood, and other liquids. Different substrates are provided for detection of different analytes. Different instruments are often required and must be calibrated for each analyte-specific test. Another problem with remote testing is that there is no way to mitigate uncertainties with test processes including results, equipment integrity, or possible miscalculation by users of test result information and what actions should be taken if any according to a given test result.

Therefore, what is clearly needed is a system for remote testing of analytes that mitigates in real time any uncertainties including user interpretation of test results.

BRIEF SUMMARY OF THE INVENTION

In one embodiment of the present invention a system is provided comprising a device for capturing biological data from a subject, a machine-readable code associated with the device, an image capturing apparatus with internet connectivity, an image processing unit to interpret the captured biological data, and an internet-connected data repository for storing the interpreted biological data.

In one embodiment the device for capturing biological data is a diagnostic strip with a biological sample from the subject placed on the diagnostic strip. Also, in one embodiment the biological sample is mixed with a reactive solution before being placed on the diagnostic strip. In one embodiment the machine-readable code is a QR code. And in one embodiment the image capture apparatus with internet connectivity is a smartphone.

In one embodiment the image processing unit operates on the internet-connected data repository's server, determining one or both of the nature of the test and a biological condition of the subject. Also, in one embodiment the server decodes the information contained in the machine-readable code and sends relevant information or instructions to the subject's smartphone based on the decoded information. Also, in one embodiment the server retains the information regarding the tests and test results conducted on the subject in a local or an internet-connected data repository. In one embodiment the smartphone executes the image processing unit, determining the nature of the test and a biological condition of the subject. And in one embodiment the smartphone, after determination, transmits the nature of the test and the biological condition of the subject to the internet-connected data repository's server.

DETAILED DESCRIPTION OF THE INVENTION

In various embodiments described in enabling detail herein, the inventor provides a remote analyte testing system that mitigates issues with remote test procedures in near real time. The present invention is described using the following examples, which may describe more than one relevant embodiment falling within the scope of the invention.

Figure 1:
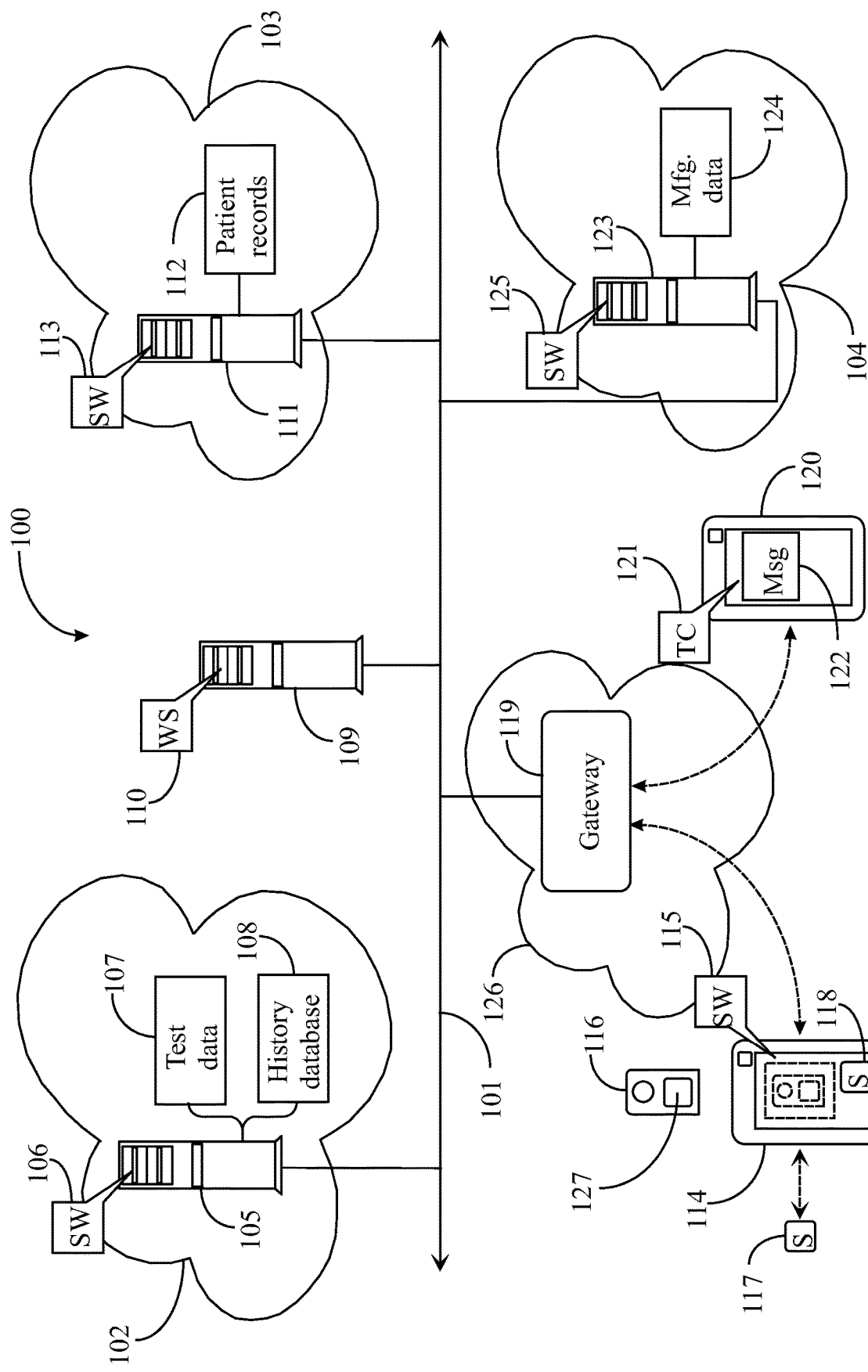
FIG. 1 is an architectural overview of a communications network supporting remote medical testing according to an embodiment of the present invention.

FIG. 1 is an architectural overview of a communications network 100 supporting remote analyte testing according to an embodiment of the present invention. Such tests are more often than not medical in nature, but other types of testing such as environmental testing or agricultural testing may also be performed using the system of the present invention without departing from the spirit and scope of the invention.

Communications network 100 includes the Internet network represented herein by an Internet backbone 101. Backbone 101 represents all of the lines, equipment, and access points that make up the Internet as a whole including connected sub networks. Therefore, there are no geographic limits to the practice of the present invention. Backbone 101 supports a web server 109 which includes a processor and memory storing all of the software and instruction required for the server to function as an Internet web server. Web server 109 hosts a web site (WS) 110 which represents an access point through which users may access the system of the invention. A user in state of access to the system is represented in this example as smart phone 114 wirelessly operated by a user and has access to server 109 through a wireless communications carrier network 126 and a multimedia gateway 119 connected to backbone 101.

Smart phone 114 may also be referred to herein as user 114 referring to the operating user of the device. User 114 may connect online and may navigate to server 109 and access WS 110 in order to register for remote testing services. WS 110 may be hosted or controlled by a service provider represented herein by a service provider domain 102 with access to Internet 101. Service provider domain 102 includes a content processing server 105 which includes a processor and at least one data repository. Software (SW) 106 is provided to execute from a non-transitory medium on the processor. SW 106 is adapted to provide, among other tasks, analysis of remote test data received at server 105 from a user, such as a user operating smartphone 114 while connected to the network. Smartphone 114 executes a software application or "thin client" (TC) application SW 115. SW 115 may be a client application of SW 106 on server 105.

Server 105 in provider domain 102 has access to a data repository 107 containing user test data that has been analyzed by SW 106 on behalf of participating users. Test data may include raw test data and associated test result data generated at the server with the aid of SW 106. Repository 107 may also contain user data such as contact and billing information, account information and device information. Server 105 has access to a data repository 108 containing a history database of test process results and follow-up data for all users of the service.

A user operating smart phone 114 may interact with a test apparatus 116 which may use a test medium or other media 127 enabled to accept a specimen for analysis. Such a specimen may be termed an analyte in other discussion in the instant specification. Apparatus 116 is at the location of the user who may perform a test. Test apparatus 116 and/or medium 127 may be items available to the user through normal consumer channels. Apparatus 116 has a region designed for accepting a medium or other medium 127 which may accept a specimen (analyte) for testing and the medium may have a machine-readable identification chip or media identification printed on the medium for identification of the apparatus and test or tests that for which the device is designed. In practice the specimen is introduced to the medium, and a reaction may immediately ensue, or there may be a mechanism for a user to initiate a reaction, such as by introducing one or more chemical compounds to the medium. As a simple example the medium may be a test medium for which a color change takes place in reaction to a specimen being placed on the medium. In this example the test medium is imaged using the still image function or moving (video) image function or a combination thereof on smart phone 114.

SW 115 may be integrated with the user's smart phone browser or other web application and may include instruction to the user regarding how test procedures are to be initiated, how to interpret test results, and what steps must occur before the test is completed. In one embodiment a set of instructions for a test may be downloaded to SW 115 on smart phone 114 from server 105 aided by SW 106 over a network connection. In this example, test apparatus 116 is depicted in camera display (broken boundary) on smart phone 114 while being imaged. The imaging will include medium 127. In one embodiment smart phone 114 may include one or more peripheral or onboard sensors such as a peripheral sensor 117 or an on-board sensor 118. Sensors 117 and 118 may take information from a user such as blood pressure, temperature, heart rate, etc. In one embodiment SW 115 may gather information from sensors 117 and 118 and may integrate that information with test information recorded by the imaging system.

Other data may also be included in data uploaded by SW 115 to server 105. These data may include GPS location information, time and date information, user identification and social profile information, identification and contact information of user-associated persons such as friends or family advocating for the health of the user, local environmental conditions and the like. In one embodiment user-associated persons might be patient advocates like family or friends, health workers, a nurse, a doctor or another caregiver treating the user. One such user is represented in this example as a smart phone 120 wirelessly connected to gateway 119 in carrier network 126.

Smart phone 120 hosts a thin client (TC) 121 in this example. Like SW 115 on smart phone 114, TC 121 may communicate with parent application 106 on server 105. A message 122 is depicted in display on smart phone 120, the message sent from server 105 regarding a test the user operating smart phone 114 is performing, has just performed, or has performed at some time in the past. The user operating phone 120 may also be enabled to perform tests using TC 121. SW 106 may also communicate on behalf of a user to third party services and data resources belonging to, or otherwise assigned to or associated with the user. For example, backbone 101 supports a medical patient network 103 including a patient records server 111. Server 111 includes a processor and at least one data repository coupled thereto and memory including all of the instruction and software enabling function as a medical network records server.

Server 111 in this example executes a software application (SW) 113, which may include an application program interface (API) linking it to application 106 on server 105 for communication. Server 111 includes a data repository 112 storing patient records and other information about patients. In this example the user operating smart phone 114 may be a patient having patient records stored in and available from server 111. In this case information from server 111 might be provided locally at smart phone 114 during collection of test and other data that reveals the URL and authentication criteria to access the patient's records. In another embodiment the user may give permission to medical network 103 to allow provider 102 to access information and communicate with network 103 as a patient advocate. Server 105 may access patient records during or after the user has initiated a particular test.

Backbone 101 in this embodiment supports a manufacturer (MFG) network or domain 104. MFG domain 104 may be a test medium manufacturing company producing test mediums like medium 127 and other test equipment, or a company that makes and sells other sorts of analytical apparatus. MFG domain 104 includes a manufacturer data server 123 that includes a processor, at least one coupled data repository, and software 125 executing from a non-transitory medium on the processor. SW 125 may include an API to link to SW 106 on server 105 for communication. Server 123 has connection to a data repository 124 containing manufacturing data for test equipment that may include test media. The data may include lot number and part number of the test media, type of test or tests for which the media may be used, expiration date of the test media, recall states for test media, any known MFG issues with the media, etc.

On each test strip medium, or alternatively on or inside the packaging or container for the medium, there is some kind of code or pattern that can be recognizable through imaging. This may be a barcode or QR code, or it might be some other distinctive pattern. Once a test is performed using the test strip medium, the result is imaged using image-capture capability of a communication device like a smart phone or a Pad device, for example, the image to be sent to the server for analysis. The image of the test comprises not only the result of the test, but also this additional information, from the coding or other distinctive pattern, which enables the server to identify the individual test. Using the coding the server can determine not only what sort of test was performed, but also the manufacturer lot number and traceability of the specific medium used in the test through the entire supply chain.

The coding or pattern that identifies the specific medium may be printed on the medium itself but might also be on the packaging or container for the medium. In some cases, the App may instruct the user to do two or more images rather than just one. By identifying the specific medium through the code or pattern, the medium may be traced by the server system to the specific manufacturer, lot number, and movement of the medium through the entire supply chain. A recall for faulty test strips may be made not usually for a whole class of tests, but rather for a specific lot number. A recall initiated by the server system after accessing data pertaining to the medium used in a test instructs the user their strip may be from a bad lot, or is past an expiration date, for example.

Test data is also processed to determine context variables, and this is described in more detail further below. From context variables, the server may provide feedback that the test is not recommended in the current environmental conditions, such as temperature, humidity, pressure, direct sunlight etc., or that, for example, a different sort of test might be more appropriate in the current context.

SW 106 is adapted to mitigate any quality issues that may come to light once a test media is identified at smart phone 114 during an imaging process. For example, when data from a test is uploaded to server 105 the data will typically, in embodiments of this invention, include the identification of the test media used. SW 106 may check the test media identification against manufacturing data in repository 124 via request to server 104 aided by software 125. If there is a quality issue with the medium, such as it is subject to a recall for example, the user may be notified via server 105 through the open network connection between smart phone 114 and server 105.

In one embodiment a user may see the test results visually as the data is being uploaded to the server. Server 105 aided by SW 106 may evaluate the test data taken from the images and any active sensors. The result might be different from any result the user perceived. In that case, the user may be immediately made aware over the network that the test result perceived by the user was not confirmed. The system might suggest that the user re-attempt the test using a fresh medium. In one embodiment a test result confirmed by server 105 aided by SW 106 is evaluated in light of current patient records and if some issue might arise from the evaluation further instruction may be sent to the user operating smart phone 114 and or to a user advocate operating smart phone 120.

In one embodiment, server 105 may consult patient records 112 through server 111 with the aid of SW 113 during a remote test procedure being performed by a user. Patient records might be accessed through permission of the user or authorized representative of the user. For example, a test result might be discovered to be affected by medication the user is taking, or it might be perceived somewhat less important or more important in light of medical procedures, surgeries, medications, nutrition regimens, or other states that might be revealed in the patient's record. Server 105 aided by SW 106 may confirm test results that are also visible to the user when the test is performed and may give feedback to the user and or one or more user advocates also connected to the network.

SW 115 on phone 114 may access the phone camera and sensors as well as contextual data, such as recent or planned activities (schedule), social context, such as who the user is with or has been with recently and what the user is doing, and user profile data including social, professional, medical, and other records that may be stored in, accessed by or connected to from the user account. Quality assurance data such as a bad lot number or test medium, and related information can be transmitted to a user during testing. Other suggestions may be sent to a user over time based on tracking user data over time or connecting user data to other data in a related context.

Chromatography is useful for testing blood glucose, or testing blood for fructosamine, creatine, and glycosolated hemoglobin HbA1c, as well as for other substances. Chromatography may be used for pregnancy tests, for ovulation tests, tests involving the prostate, tests involving body fluids, including fecal matter and breath. Chromatography may be used in alcohol and drug testing. In one embodiment the present invention employing image capturing and image transmission to remote equipment might be used in a context not limited to a user. For example, tests may be implemented to test water quality in a pollution monitoring embodiment, or to test the quality of foods and drinks. Air quality tests and soil testing may also be performed. Other types of tests might include gas, liquid, high pressure liquid, or material that can shed ions, paper chromatography, gas chromatography, thin-layer chromatography, absorption chromatography, partition chromatography, ion exchange chromatography, molecular exclusion chromatography, and affinity chromatography.

Figure 2:
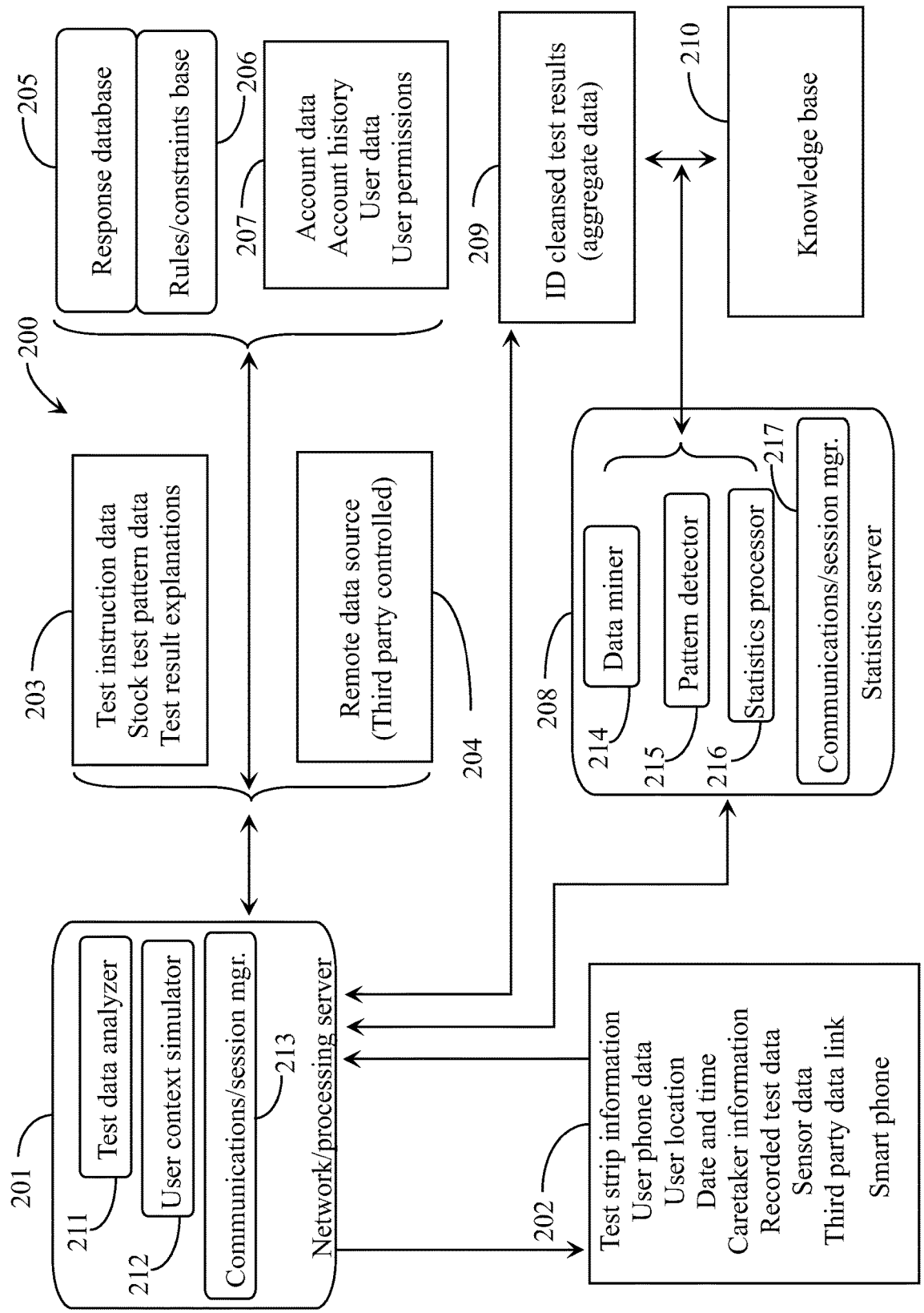
FIG. 2 is a block diagram depicting interaction between various components of a remote medical testing system.

FIG. 2 is a block diagram 200 depicting interaction between various components of a remote testing system. Diagram 200 includes a network-connected processing server 201 analogous to server 105 of FIG. 1. SW executing at the server may include a test data analyzer 211 adapted to read raw test data uploaded from the phone and to determine quality and accuracy of a test result. In one embodiment software may include a user context simulator 212. While not required to practice the invention, a context simulator such as simulator 212 may be provided with the application to analyze contextual data uploaded from the user's phone or accessed from a source linked to the user's account. As an example, it may be that the user has diabetes, and according to test results has very high blood sugar. The user's calendar may note a birthday celebration for the user. The system may take this information into consideration in light of the test result and issue an alert to one or more associates of the user informing them of the result and suggesting that no sugar such as cake, ice cream, etc. be consumed by the user at the celebration.

Server 201 may include a communications session manager 213. Communications session manager 213 may be part of normal server session management software and may include functionality such as data messaging and voice calling software so that any important information may be immediately conveyed to the user and or to at least one user advocate or associate. A smart phone 202 is depicted herein and is analogous to phone 114 of FIG. 1. Phone 202 has a network connection to server 201.

Information uploaded from the phone may include test medium identification information, such as lot number, test type, etc., user phone information, user current location, the date and time, user advocate or primary caretaker data (name, contact, and role). This information may, in one embodiment, be stored separately from the user's smart phone. Such data may be added to the user account during or after the registration process and may not actually be on the user's telephone. In another embodiment a user may add such data to the application on the phone and upload it to the server during a next test procedure or otherwise at any time. Other information uploaded to server 201 from phone 202 may include recorded test data, any relevant sensor data, and any third-party data links the user wishes to include in the user network of persons involved with advocating the user's continued health.

Server 201 has access to data repositories such as repository 203 storing test-specific instruction to the user, stock test pattern data for confirming and validating test results, and test result explanations associated with specific test types. Server 201 has access to a repository 204 representing a remote data source controlled by a third party. It might be a social interaction service having data about the user such as a profile, a list of friends, and scheduled activities.

Server 201 has access to a database 205 storing preformulated system responses that can be sent to users in the form of either text messaging or voice telephone calls. In one embodiment there are generic system responses such as a response to a blood sugar test that reads too high, such as "It is recommended to avoid all sweets for the next 24 hours". In one embodiment a system response might be generated dynamically according to a test result and related contextual information analyzed in light of the result. System responses may be text messages, emails, posts, or system recorded voice messages that may be left in voice mail or enunciated over an open telephone connection. System responses may be built from generic templates without departing from the spirit and scope of the present invention.

Server 201 has access to a repository 206 storing rules and constraints relative to testing and forming system responses to users and or user advocates. Each test type may have its own set of rules and constraints relative to testing and responding to users and others over the network. Server 201 has access to a data repository 207 containing other relevant data such as user account data, user history, personal user data, user permissions for sharing data, etc.

In one embodiment of the invention, server 201 has access to a statistics server 208. In one embodiment user test result data may be cleansed of all personal information and deposited into an accessible data repository, such as repository 209, storing cleansed test results in aggregate. Each testing event may be aggregated with other events for the purpose of data mining to detect patterns, create statistics, and to use the information to improve or to fine tune the software application and service. A data cleansing application may remove all personal information from records so that each event is essentially a john doe. The aggregate of the data is then mined for information.

Server 208 includes a processor and memory storing all of the software and instruction required to function as a statistics server. Server 208 may be hosted by the service provider or by a third party without departing from the spirit and scope of the present invention. A data cleansing application (not illustrated) may be provided to server 201 so that the data from users can be aggregated for mining in repository 209. Server 201 has direct access, in one embodiment, to repository 209 and to a knowledgebase 210. Server 208 may access repository 209 and mine the data stored in that depository. To this end, SW on server 208 may include a data mining application 214. A pattern detector application 215 may be provided on server 208 to detect certain patterns in test results that may emerge in comparison with other data, like location information, manufacturing data, or other data that might be included with test data.

Server 208 includes a statistics processor 216 to compute statistics for certain detected data patterns related to the aggregate of users taking a particular test, for example. Different combinations of data may be mined, such as all data for a specific test type taken by users in a specified region. Data may be broken down more granularly, such as all test data from a particular test and using a particular manufacturer's test medium. Information gleaned from the data mining and statistics generation might be leveraged to create new test constraints or instructions sent to user applications. The information may also be leveraged to tailor system responses for users engaging in future tests if their uploaded data is flagged by demographics or other issues common to the mined cases effecting the response change for those users.

Server 201 has access to a data repository 210, which may contain a knowledge base built over time with articles or summaries of known issues with test procedures, test media, or other technical data or issues regarding software installation and procedures. In one embodiment a user may remotely access data from knowledge base 209 by requesting it from server 201. Server 201 may update or make changes to the data in repository 210 as statistics warrant such changes. In one embodiment knowledge created through mining the identity-cleansed data may be shared with other interested parties, such as with test media manufacturers, to help improve products and services. It is noted that the system of the present invention may be integrated with existing third-party applications, like a health network of patients and health care workers, without departing from the spirit and scope of the invention.

Figure 3:
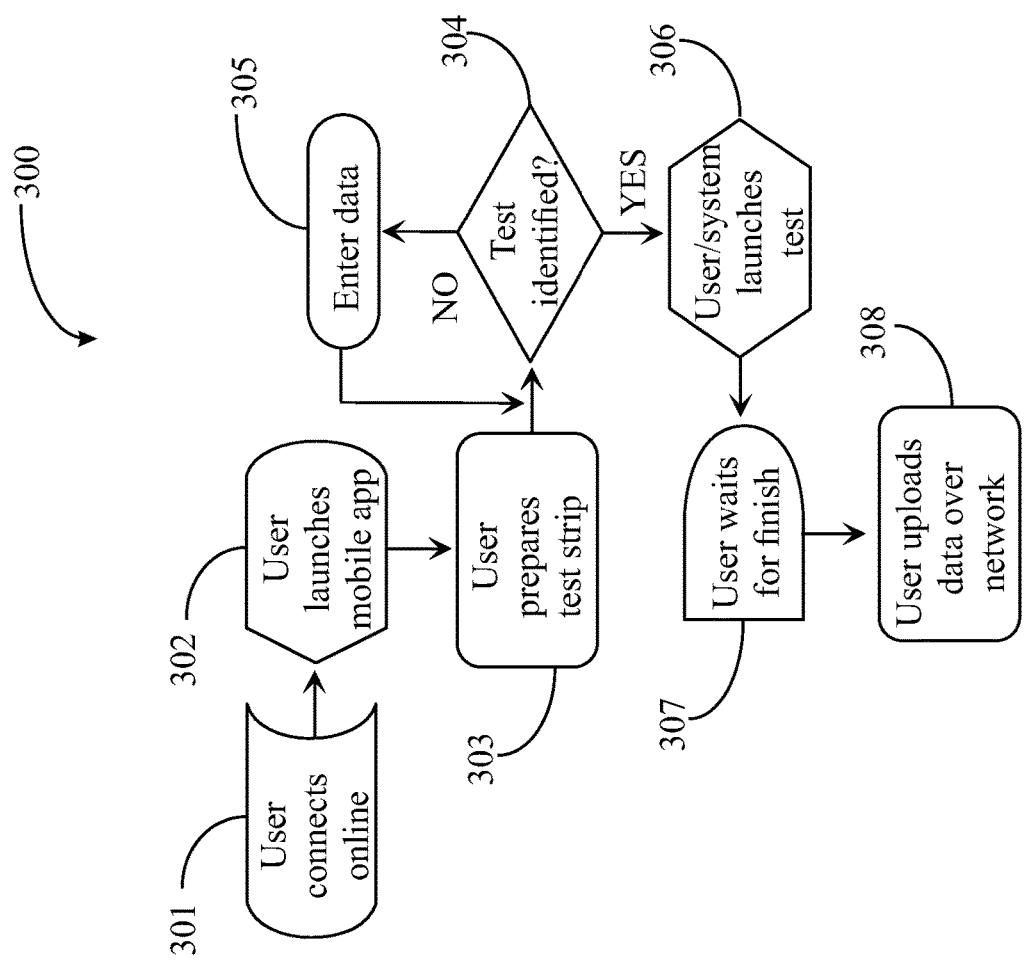
FIG. 3 is a process flow chart depicting steps for executing a remote medical test process according to an embodiment of the present invention.

FIG. 3 is a process flow chart 300 depicting steps for executing a remote test process according to an embodiment of the present invention. A user with a smart phone analogous to operating smart phone 114 of FIG. 1 may connect online at step 301 for the purpose of initiating a remote test procedure. It is assumed in this example that the user is registered with a service provider and has downloaded and installed a client application (mobile application) for acquiring the test data.

The user launches the mobile application at step 302 in preparation for initiating the test while connected to the service. In this step the user may select a test type and is assumed to be in possession of a test medium usable for the type of test selected. In step 303 the user prepares the test medium for testing according to instruction for the type of test to be undertaken. This may include how to place the specimen for testing on the substrate. The user may record one or more images and or video clips of the reaction of the test medium once a specimen for testing has been introduced.

During test medium imaging, the test type may be identified at the server. The system might determine, as soon as imaging data is received at the server, whether the test may be identified or not. If the imaging process for some reason fails to identify the test type at step 304, the user may be required to enter supporting data at step 305. If the system identifies the test type at step 304, the test may be initiated at step 306. It is important to note that the test may be underway or completed locally before the system actually identifies the test type or receives any data. It is also possible that the user will identify the test type manually, including confirming the proper test medium to use, before the medium is prepared with a specimen. In one embodiment a user may take an image or scan the test medium before a specimen is introduced in order that the system may determine by MFG data the test type and instruction required, and send that information back to the user over the network connection before the user proceeds.

In one embodiment the system may, in the background, check a MFG site once the test medium is identified to determine if there are any known issues with the medium or its use that may cause test failure or inaccurate test readings. The user may be given a message or call in the event of an expired or otherwise quality compromised test medium. There may, for example, be a current recall of the test medium. The test medium may be obsolete and may be require replacement by another test medium before the test is initiated.

In step 307, the user waits for the local test reaction to finish. In this step the user may or may not be able to determine the test result visually before recorded data is uploaded to the server. The term server as used in this context represents a server analogous to server 105 of FIG. 1 or server 201 of FIG. 2. The test reaction images and or video are uploaded to the server in step 308. The process flow covers test initiation and result recording and server upload of all of the required data. The process flow switches to the server once the user data is obtained.

Figure 4:
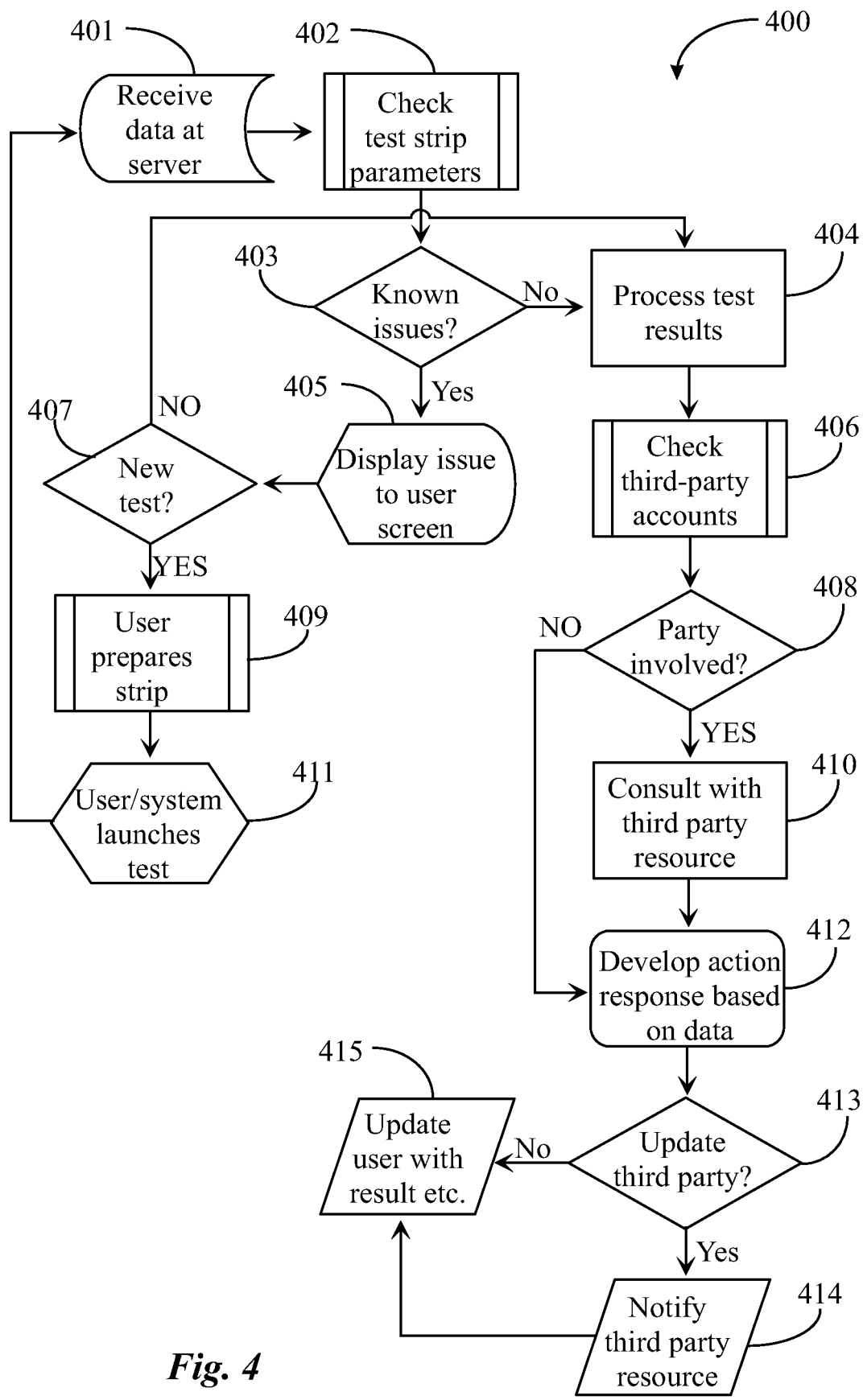
FIG. 4 is a process flow chart depicting steps for remote mitigation of test data received from a remote medical test process.

FIG. 4 is a process flow chart 400 depicting steps for remote processing of test data received from a remote medical test process, as described with reference to FIG. 3 above. A server analogous to server 105 or server 201 (FIG. 1, FIG. 2) receives the test data from a user. Step 401 represents a step after step 308 of FIG. 1. The server may receive recorded test data presented as one or more images showing test reactions. The images or video may be time stamped when recorded. The combination of images or video recorded might vary widely among available test types. Some procedures may include sensed data coming from peripheral or onboard sensors. At step 402 the system checks test medium parameters associated with the test for which data is received at step 401.

Once a test medium is identified to the system at step 402, the server might check if there are any known issues with the test medium at step 403, such as whether the medium is past an expiration date or is from a lot determined to be faulty. The server may consult with manufacturing information held locally or remotely to validate the test medium. In one embodiment, a test medium must be validated for expiration and any other known issues before processing of test data might occur. If the system finds at step 403 any issues with the test medium this might negate or compromise any useful test result, the system may send an alert notifying of the issue or issues, the notification displayed for the user in step 405. In this case, the system may also determine at step 407 whether a new test must be initiated.

In an embodiment of the invention the imaging of a medium once a test is performed is not solely for the purpose of analyzing a test result at the server, although this is certainly an important issue. There are three sets of information sent in or with the image sent to the server. One is the test result. A second set of information is the coding associated with the specific medium, which may be, as described above, a bar code, a QR code or may be some other pattern. This coding identifies the specific medium used, and may be used by the server to determine the viability of the medium for the test performed. Whether the test is valid or may be faulty for any one of several reasons, such as a medium past an expiration date, a medium that has previously been determined to be faulty, and is subject to recall, and so on.

The third set of critical information to accompany the image of the test is contextual. This is a critical distinguishing issue in embodiments of the present invention. Data sent along with the image may include geographic location, temperature at time of test, altitude at the test location, air pressure at test location, humidity at test location, weather patterns at or near the test sites, lighting patterns at test sites, and more that may be determined by sensors, or by input by a user.

Considering the test result as imaged, the medium identification as imaged, checked against know data, and the contextual information accompanying a test image, a great deal of nuance and helpful guidance is provided in embodiments of the invention.

If it is determined a new test should be performed at step 407, the user may prepare a new test medium at step 409. The user/system may perform the testing on the new medium in step 411. The process may then resolve back to step 401. The new test procedure may include all of the steps of flow chart 300 of FIG. 3 after step 302. If it is determined at step 407 that an issue, while important to the user, may not compromise the test, the process may resolve to step 404 where the server application processes the recorded test data including any local test results recorded.

If at step 403 there are no known issues with the test medium the original test results are processed at step 404. The system may then check in step 406 if the user has previously identified any other accounts where data might be accessed according to permission from the user.

If it is determined that there are no third-party accounts the user has granted permission to access, the process may skip over to step 412 where an action response including confirmed test result is developed based on analyzing the test result data and other data sent from the user. If the user has accounts but has not linked them to the service, the system may inform the user that linking to certain accounts may help to optimize services for the user and for other users through data mining as described previously.

If one or more third party accounts are involved (linked) in the information loop surrounding the test process, and permission has been granted to access data from these accounts, the system may consult with those accounts at step 410. Additional data garnered from these accounts may be used to refine the test result information and to help generate a response action more tailored to the particular user's current situation at step 412. At step 413 the system may determine whether the third-party account accessed in step 410 should be updated with the test results and action plan for the user.

If at step 413 it is determined that the parties need not be updated with the test result or data surrounding the system response formed in step 412, the process moves to step 415 where the user is given the test result confirmation over the network and, if warranted, the response including any suggested actions. In one embodiment, responses may include advertising by other product and service providers related to the industry. For example, the test medium being imaged may be more expensive than another competing medium that has the same quality rating. In one embodiment, a user consistently failing a repeated remote testing procedure may be advised to go to rehab, for example, with one or more local and system-approved rehabilitation centers advertisements being displayed for that user.

If it is determined at step 413 the one or more third parties should be updated, the updating may occur at step 414 before or during the time the user is updated. The update to a third-party account might include a test result and any system suggestions to be provided to the user including suggestions for consulting a doctor, etc. The advance notification to the third party may help get the user an appointment in a more timely fashion than relying on the user to set his or her own appointments. It is also noted herein that third parties may also include caretakers or user advocates like family and friends.

Figure 5:
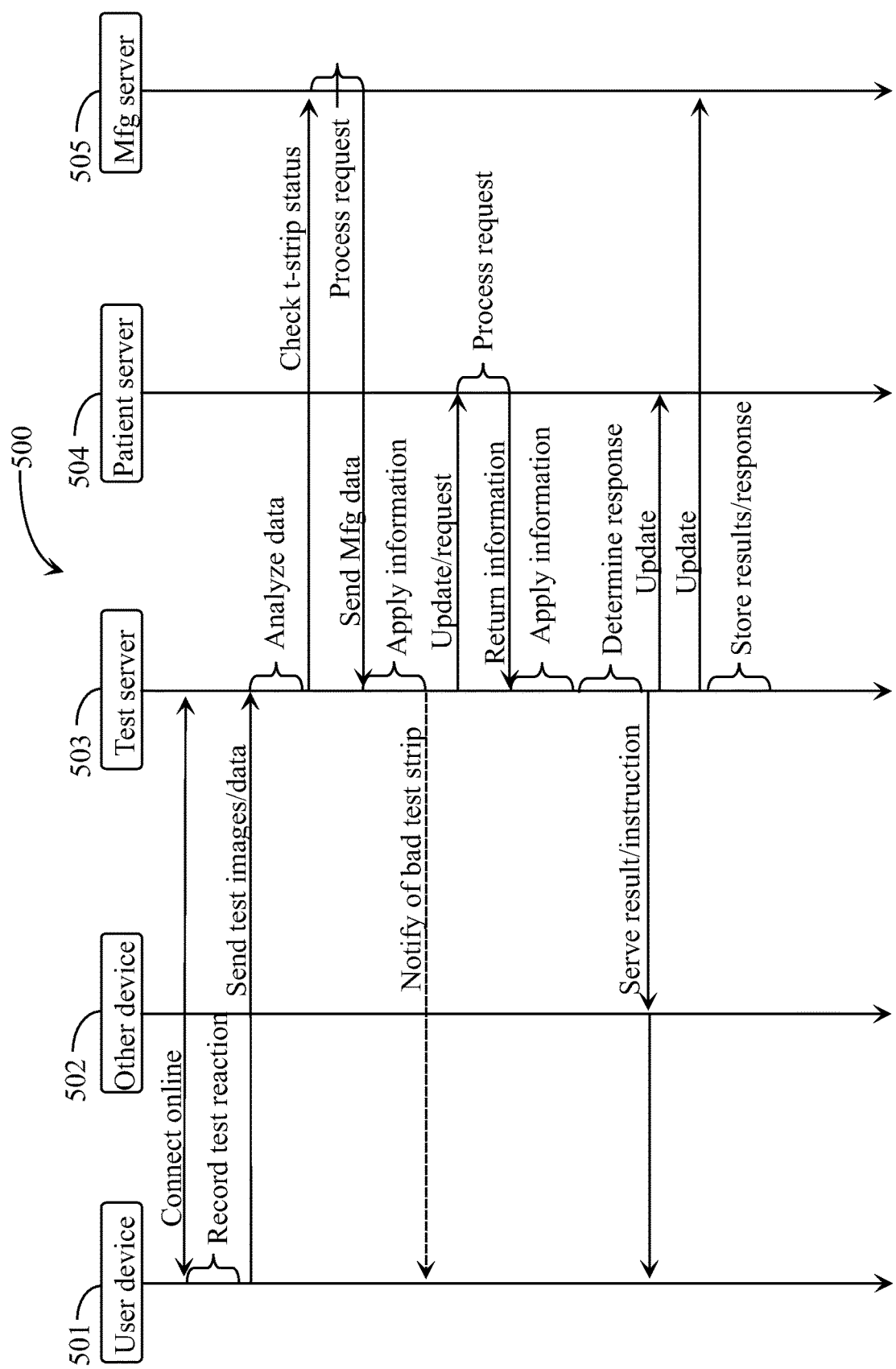
FIG. 5 is a sequence diagram depicting interaction between various components according to another embodiment of the present invention.

FIG. 5 is a sequence diagram 500 depicting interaction between various system components according to an embodiment of the present invention, with process flow analogous to the flow diagram of FIG. 4, but also indicating the communication between the different nodes in the system. In this example, the registered user operating a user device 501 (smartphone with application) has a user advocate operating another smartphone (other device with application) 502. The user also has a patient records account accessible by permission through a patient records server 504. In one embodiment the patient server includes an application or application program interface designed to enable it to work with the service.

In interaction, the user operating device 501 may connect online with a test server 503, the test server analogous to server 105 of FIG. 1. It is noted that there may be more than one test server available for interacting with the user without departing from the spirit and scope of the present invention. In this interaction, the user operating user device 501 makes a connection over the network with the test server 503. The user launches the mobile application, prepares a test medium and records the subsequent analyte test reaction. In one embodiment, the test medium might be validated by the system before preparing the medium with a specimen. This may be critical in some cases where the specimen comprises a small amount of material.

The recorded images and or video documenting the test reaction and result are sent to server 503 from user device 501 while in session. In one embodiment, the user might prepare and run a test while offline and then connect with server 503 to upload the recorded information. Server 503 receives the recorded data and other information relative to the situation and user. The server with the aid of SW analogous to SW 106 of FIG. 1 analyzes the data. In one embodiment the local application has recorded the test result and the server application confirms or validates the result. In one embodiment, the local application does not interpret the test result rather, it is determined at the server from the recorded raw data.

In this interactive sequence, test server 503 sends a request to access test medium manufacturing data from a manufacturer server 505 analogous to server 123 of FIG. 1. The server processes the request and makes the data available. It is assumed that the server received manufacturer information during imaging of the test medium documenting a test reaction. However, in another embodiment the test medium might be validated for a test prior to the user preparing the medium with a specimen and actually imaging the reaction. The MFG information is applied to the process of vetting the test results. In one possible instance the test medium used to host the analyte reaction may have been compromised in a way that renders any test results unusable. In this case server 503 may notify the user operating device 501 of the issue such as a bad test medium. A test medium might be part of a current recall or it might be contaminated, broken, or expired.

In the event of a clean bill from the manufacturer regarding the integrity of the test medium, server 503 might send a request to a patient records server 504. Server 504 is analogous to server 111 of FIG. 1. Server 504 may validate and process the request under permission granted by the user. The patient records server may return the data requested to server 503. The patient data may be applied to the process and may affect how the system responds to the user. Server 503 determines a response action after considering all of the data at the end of the process. Once a response is determined, server 503 sends the test result confirmation, and suggested action or course to the user operating device 501 and to a user advocate operating device 502. Server 503 may also update the third-party data sources involved such as server 504 and server 505.

An update to a patient records server may be just the user identification, the test results, and the response action suggested to the user by the system. In one embodiment the suggested action may be to make an appointment with a doctor, and the update to the patient records server may be a request for the user's health network or office to contact them to schedule the suggested appointment. An update to MFG server 505 might be an accounting function adding to the number of instances that users of the service are using a particular test medium provided by that manufacturer. Server 503 may store results and other associated data in a data repository adding to a history file of the user's test activity.

There may be more or fewer third-party servers involved in the testing process for a user without departing from the spirit and scope of the present invention. There may be more than one user advocate to which user information might be shared without departing from the spirit and scope of the invention. Such advocates might include coaches, family members, friends, supervising agents, managers, healthcare workers, and so on.

In one embodiment social context data uploaded from a user device like device 501 or accessed from a user account like a Facebook™ calendar, for example, could affect what type of response action is suggested to the user by the service provider. A response action might be a suggestion that the user not attend a planned three-day conference after getting a particular test result that may require other action such as obtaining a specific medication before a condition deteriorates. Responses from the system may contain other suggestions, instructions, etc. that may be predisposed to the test results and any extenuating information learned during the process.

Figure 6:
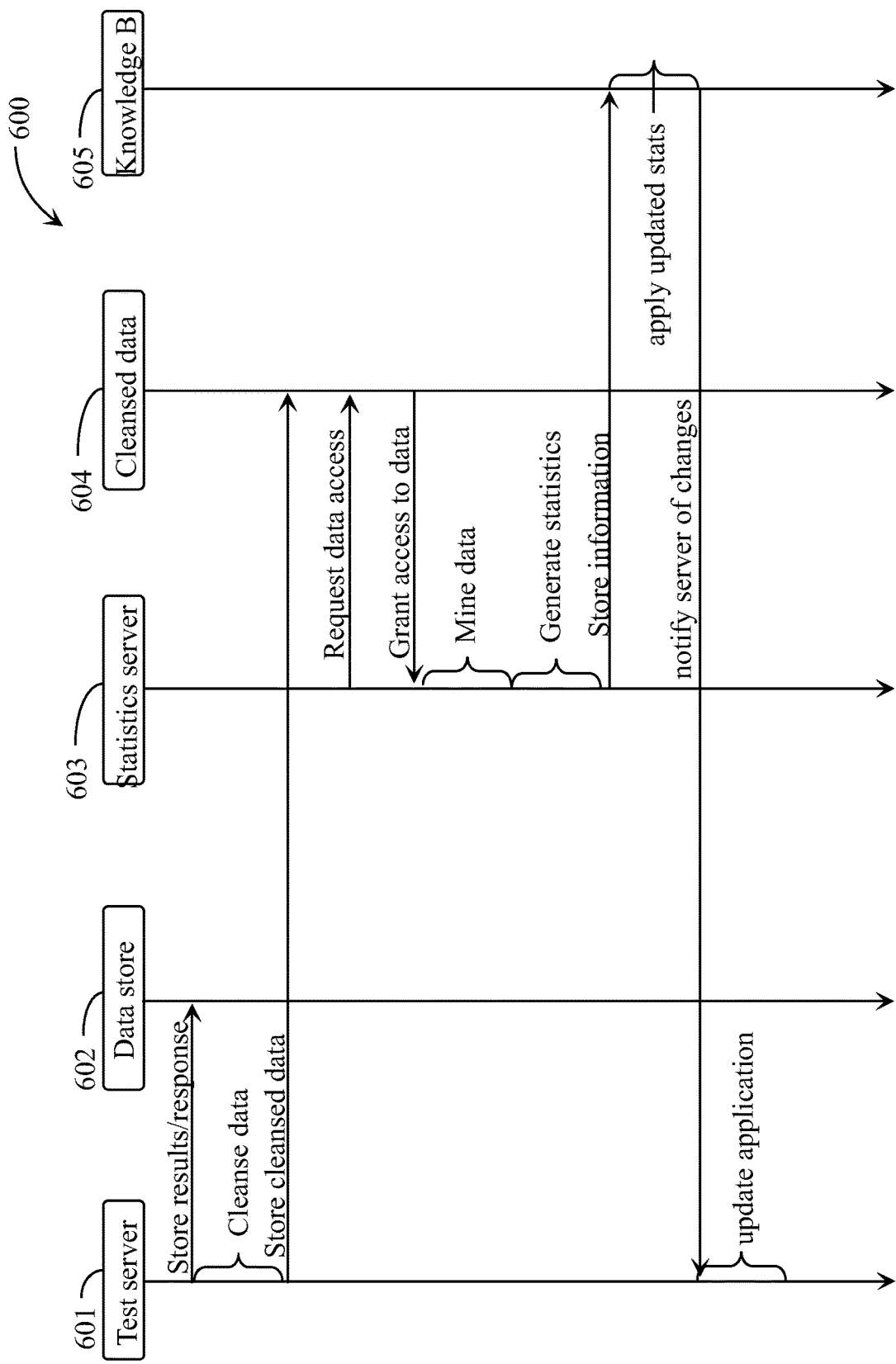
FIG. 6 is a sequence diagram depicting a process of mining received test data for statistical information.

FIG. 6 is a sequence diagram 600 depicting a process of mining test data for statistical information. In this interaction sequence a test server 601 analogous to server 105 of FIG. 1 stores user test results and records of any suggestions, instruction, or other actions taken on behalf of the user in a data repository 602. Repository 602 is analogous to repositories 107 and 108 of FIG. 1. This may be done on a continuing basis with any and all users accessing the service.

Server 601 may cleanse personal data from the data sets for each user and store the aggregate information in a data repository 604 (cleansed data). This may also be done on a continuing basis. A statistics server 603 analogous to server 208 of FIG. 2 may request access to the cleansed data from repository (server) 604. Server 604 may grant access to the data to server 603. Server 603 may mine the accessed data for patterns that might be relevant to test medium integrity, test result thresholds for specific tests, or other patterns in the test data that depict usage trends for certain demographics or for certain geographic areas, and so on.

Server 603 may identify issues raised by the repeating patterns and may generate current statistics relative to emerging trends or issues. In one embodiment statistical data may be stored in a knowledge base 605 analogous to knowledge base 210 of FIG. 2. Existing data in the knowledge base may be replaced or amended to reflect new findings or trends. In one embodiment statistics may be included in and updated in knowledgebase articles made available to users and user advocates by request or search from their mobile devices.

In one embodiment if the statistical data identifies one or more issues with current test processes or equipment that should be addressed, the knowledgebase server 605 may notify test server 601 of changes. The test server application and distributed client applications may be updated with recommended changes supported by the results of mining the aggregate data.

Figure 7:
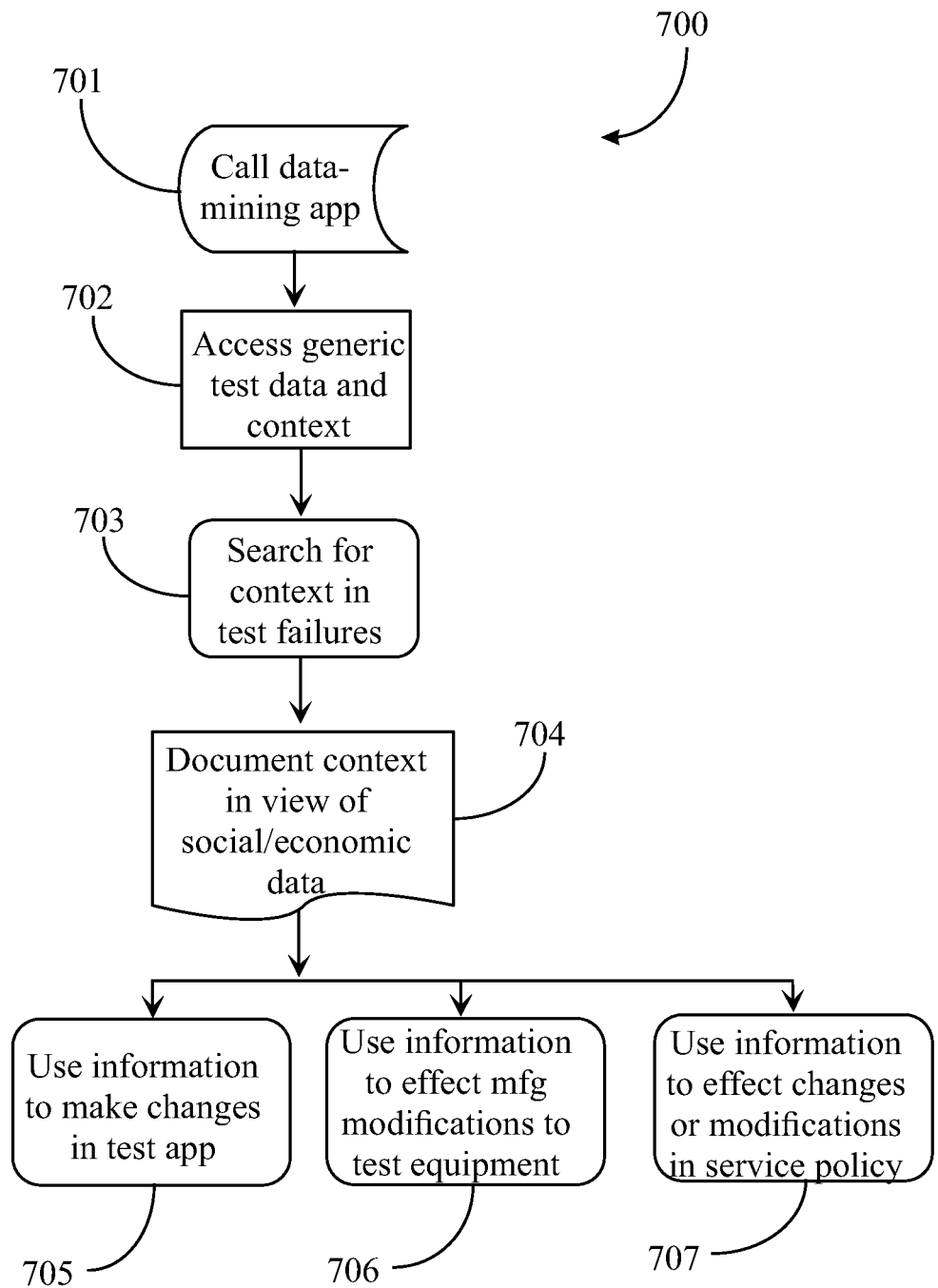
FIG. 7 is a process flow chart depicting steps for using knowledge discovered through data mining according to an embodiment of the present invention.

FIG. 7 is a process flow chart 700 depicting steps for using knowledge discovered through data mining according to an embodiment of the present invention. In step 701 a data mining application is executed from a server such as a statistics server having access to a data source containing test result data cleansed of personal association and information. The data is accessed by the mining application in step 702.

In step 703 a pattern detection algorithm searches for context in test failures, for example. The test failures may be those of a particular test type found by mining all test failures then identifying patterns in failures that may be associated by such as location, temperature at time of test, altitude at the test location, air pressure at test location, humidity at test location, weather patterns at or near the test sites, lighting patterns at test sites. These associations of test failures provide and record a common thread establishing a pattern or trend as context. In step 704 the system may document or record context for the patterns detected. Context is determined by considering social/economic data that may be shared between test failure cases in a cluster. Mining test failure data is just one example of a category of the data where there may be patterns discovered that may be contributing to the failure rate or frequency. Other categories of data may be mined to look for patterns emerging in those categories. Data might be mined for a test type that might include test mediums from different manufacturers. A pattern might emerge that single out a particular brand of test medium.

At step 705, the system might use information developed from data mining and pattern identification to suggest or make changes or modifications in the testing application distributed to user devices. At step 706, the system may use the information to effect manufacturer modifications or changes to test equipment including test mediums. At step 707, the system might use the information to effect changes or modifications to service policy.

In some embodiments the user may interpret the chromatography result with the eye or with a color chart and may also have confirmation and validation of a test result by another "set of eyes", namely the system application. In some embodiments users do not interpret test results and in others some test results might be interpreted locally while other test types are processed at the server using the recorded information from the mobile application.

The system of the invention may provide a variety of test types that may be performed in a single equipment configuration somewhat standardizing the testing process in general and reducing dependency on specialized peripheral test equipment like cassettes and the like. Tests may be provided for testing any bodily fluid like blood, urine, stool, sweat, mucus, semen, and pus. Testing may be designed for drug and alcohol detection, forensics and crime identification, dye composition in fibers, environmental concerns (PCBs in fish, lead in water, pollution), food systems and tracing, detecting chemicals and pesticides, insecticides, residues in food plant and soil health, and need for more/less water, fertilizer, pregnancy and ovulation, bomb detection, and other chemical and biological agents, separating amino acids and anions, RNA fingerprinting, testing histamines, and antibiotics.

The system communicates recall information to help trace defective or expired test mediums and provides near real-time feedback to the user regarding current recalls or identification of bad test mediums. The software may be periodically updated with new test mediums and manufacturers. New or altered interpretations of test results may be developed from information developed from processing the aggregated data collected from the users and cleansed of personal data.

The system application on the server is enabled to look at resulting color patterns, resulting distance traveled in a substrate, or indications of presence or absence of an analyte. In one embodiment enabling recording of motion video, the system can use test reaction time as an input to pattern detection. In one embodiment a test medium might be utilized for more than one test or test type. Multiple tests can be combined on one substrate providing convenience to the user with improved pattern detection as the patterns analyzed in the server include more features of the data.

The feedback mechanism to the user has several functions. It may provide notifications that a test medium is defective or has expired, which can be vital quality assurance in near real-time particularly for medical tests. It may also provide an audit trail for all tests so that quality issues and patterns can be detected over time. By combining the contextual information with test result information, quality issues can be associated with variations in context and user profile data. For example, the system may detect that certain issues occur more frequently in women than men, or that certain issues occur more frequently in different locations or climates, or times of day. The system may detect patterns that may be useful for test quality assurance but also for use of data and how to guide the user based on the test results through the environmental data taken from sensors tethered to, wirelessly connected to, or onboard a smart phone including orientation data, vibration data, location data, altitude, pressure, temperature, lighting, time of day, etc.

In some embodiments of the invention, patterns in test results or test quality in association with environment and context can be learned by the system. This may be in some embodiments a machine learning process, not unlike a spam filter. Each test strip and resulting image and the contextual data comprise a vector of attributes. When a failed test is identified, user reported error is received, or an unexpected result is determined across perhaps thousands of tests, such problems may be associated contextual data. Some tests have a fail-safe built into the chromatography, wherein specific patterns emerge if the test looks like it has failed. For example, if the fail-safe aspects of the medium are seen, or if the users are consistently reporting failures or mismatch between the visual calibration, or if we quality assurance tests check consistency with other more traditional test devices, rules for "bad test" or "likely bad test" may be developed, and may be integrated with or provided as algorithms known and used for filters among other machine learning examples. In reference to the supply chain, that the user got the medium from a certain retailer served by a certain distributor, it may be discovered that the environmental problem is not with the user but with the distributor who might have left the lot of media in an environment that disturbed the medium, such as getting too hot or cold or too humid, for example. An important point is that associations and patterns may be developed by machine-learning techniques that can find problems and even predict problems developing or likely to occur.

In another aspect of the invention augmented reality technology may be used to facilitate the operation of the system. In embodiments thus far described above a system is provided having a measuring device providing a quantitative output of a physiological condition of a subject, a non-transitory identifier affixed to a surface proximal to the measuring device, an imaging apparatus having an Internet connection, and an internet-connected server coupled to a data repository, the Internet-connected server executing coded instructions on a processor. The physiological measuring device is engaged, providing a quantitative indication of the physiological condition of the subject, an image of the readout and the non-transitory identifier is initiated by a user, and the captured image is transmitted to the internet-connected server. The identifier must be produced and applied to the medium, the packaging or to another surface, and a user must initiate an image capture to transmit the identifier to the server.

In an alternative embodiment of the invention image recognition may be used to identify both the device and the subject prior to sending the needed information to the web server. In this embodiment of the invention the barcode or QR code is not needed. The subject's cell phone has an image recognition module trained and enabled to recognize the physiological measuring device. Referring back to FIG. 1, in this unique embodiment of the invention device 116 provides a readout of a quantitative value as a result of a test of a medium.

In operation the subject may place a sample in the device, which analyzes the sample and provides the readout, being a quantitative value of a physiological condition of the subject. The subject images the device with the camera of cell phone 114, executing an application (SW 115) which leverages the image recognition capability to identify the device, providing information as to the nature of the analysis. The readout is captured in the same image, and the application in one embodiment performs Optical Character Recognition (OCR) on the readout portion of the image. The identity of the subject may be provided by the identification of the cellular telephone belonging to the subject, or the identity may be programmed into the app. The App then causes the gathered and interpreted information to be sent to the server. The server gets the subject ID, the value of the readout, and the nature of the device.

In another embodiment there may be a user identification module active on the imaging device, whereby a user associated with the cell phone may provide an alternative identification for the subject who is being tested. There may be on the cell phone a library of subjects which the user may browse to select the ID of the subject for which a sample may be analyzed by the measuring device.

In an alternative version the subject images the device, including the readout, and the image is sent to the server along with the subject ID, and the image recognition and OCR of the readout occur at the server. The server has the subject's profile stored in one or more data repositories at the server.

It will be apparent to one with skill in the art that the remote analyte detection system of the invention may be provided using some or all of the mentioned features and components without departing from the spirit and scope of the present invention. It will also be apparent to the skilled artisan that the embodiments described above are specific examples of a single broader invention that may have greater scope than any of the singular descriptions taught. There may be many alterations made in the descriptions without departing from the spirit and scope of the present invention.

It will also be apparent to the skilled person that the arrangement of elements and functionality for the invention is described in different embodiments in which each is exemplary of an implementation of the invention. These exemplary descriptions do not preclude other implementations and use cases not described in detail. The elements and functions may vary, as there are a variety of ways the hardware may be implemented and in which the software may be provided within the scope of the invention. The invention is limited only by the breadth of the claims below.

The invention claimed is:

1. A system comprising:
    a device for capturing biological data from a subject;
    a non-transitory machine-readable medium that stores a computer program having a program code associated with the device;
    an image capturing apparatus with internet connectivity;
    an image processing unit to interpret the captured biological data; and
    an internet-connected data repository for storing the interpreted biological data.

2. The system of claim 1, wherein the device for capturing biological data is a diagnostic strip with a biological sample from the subject placed on the diagnostic strip.

3. The system of claim 1, wherein the biological sample is mixed with a reactive solution before being placed on the diagnostic strip.

4. The system of claim 1, wherein the program code is a QR code.

5. The system of claim 4, wherein the image processing unit operates on the internet-connected data repository's server, determining one or both of the nature of the test and a biological condition of the subject.

6. The system of claim 5, wherein the server retains the information regarding the tests and test results conducted on the subject in a local or an internet-connected data repository.

7. The system of claim 6, wherein the smartphone, after determination, transmits the nature of the test and the biological condition of the subject to the internet-connected data repository's server.

8. The system of claim 4, wherein the server decodes the information contained in the program code and sends relevant information or instructions to the subject's smartphone based on the decoded information.

9. The system of claim 4, wherein the smartphone executes the image processing unit, determining the nature of the test and a biological condition of the subject.

10. The system of claim 1, wherein the image capture apparatus with internet connectivity is a smartphone.

* * * * *